United States Patent
Sato et al.

(10) Patent No.: US 10,876,140 B2
(45) Date of Patent: Dec. 29, 2020

(54) METHOD FOR PRODUCING POLYHYDROXYALKANOIC ACID, AND MICROBES

(71) Applicant: KANEKA CORPORATION, Osaka (JP)

(72) Inventors: Shunsuke Sato, Takasago (JP); Hisashi Arikawa, Takasago (JP); Rina Aoki, Takasago (JP)

(73) Assignee: KANEKA CORPORATION, Osaka (JP)

(*) Notice: Subject to any disclaimer, the term of this patent is extended or adjusted under 35 U.S.C. 154(b) by 0 days.

(21) Appl. No.: 16/471,267

(22) PCT Filed: Dec. 20, 2017

(86) PCT No.: PCT/JP2017/045772
§ 371 (c)(1),
(2) Date: Jun. 19, 2019

(87) PCT Pub. No.: WO2018/117168
PCT Pub. Date: Jun. 28, 2018

(65) Prior Publication Data
US 2020/0109423 A1    Apr. 9, 2020

(30) Foreign Application Priority Data
Dec. 20, 2016 (JP) .................. 2016-246635

(51) Int. Cl.
*C12P 7/62* (2006.01)
(52) U.S. Cl.
CPC .................... *C12P 7/625* (2013.01)
(58) Field of Classification Search
None
See application file for complete search history.

(56) References Cited

PUBLICATIONS

Raberg et al., "Ralstonia eutropha H16 Flagellation changes according to nutrient supply and state of poly(3-hydroxybutyrate) accumulation", Applied and Environmental Microbiology 74(14): 4477-4490 (Jul. 2008). (Year: 2008).*
International Search Report dated Mar. 27, 2018 in PCT/JP2017/045772 filed on Dec. 20, 2017.
Zheng, Q. et al., "*Paracoccus beibuensis* sp. nov., Isolated from the South China Sea", Curr Microbiol, 2011, vol. 62, pp. 710-714.
Burdman, S. et al., "Aggregation in *Azospirillum brasilense*: effects of chemical and physical factors and involvement of extracellular components", Microbiology, 1998, vol. 144, pp. 1989-1999.
Anderson, A. J. et al., "Biosynthesis and composition of bacterial poly(hydroxyalkanoates)", Int. J. Biol. Macromol., 1990, vol. 12, pp. 102-105.
Sato, S. et al., "Regulation of 3-hydroxyhexanoate composition in PHBH synthesized by recombinant *Cupriavidus necator* H16 from plant oil by using butyrate as a co-substrate", Journal of Bioscience and Bioengineering, 2015, vol. 120, No. 3, pp. 246-251.
Insomphun, C. et al., "Improved artificial pathway for biosynthesis of poly(3-hydroxybutyrate-co-3-hydroxyhexanoate) with high $C_6$-monomer composition from fructose in *Ralstonia eutropha*", Metabolic Engineering, 2015, vol. 27, pp. 38-45.
Extended European Search Report dated Jul. 7, 2020 in European Patent Application No. 17884387.6, 9 pages.
Anthony J. Sinskey, "Engineering *Ralstonia eutropha* for Production of Isobutanol (IBT) Motor Fuel from Carbon Dioxide, Hydrogen, and Oxygen," Massachusetts Institute of Technology Project Final Report, XP055707100, Dec. 16, 2013, pp. 1-105.
Kaspar P. Locher, "Structure and mechanism of ATP-binding cassette transporters," Philosophical Transactions of the Royal Society B, vol. 364, XP055707239, 2009, pp. 239-245.

* cited by examiner

*Primary Examiner* — Anand U Desai
(74) *Attorney, Agent, or Firm* — Oblon, McClelland, Maier & Neustadt, L.L.P.

(57) ABSTRACT

Provided is a method for producing PHA by a microbe with improved productivity of PHA, and a PHA-producing microbe used for the production method. A method for producing polyhydroxyalkanoic acid, the method including a step of culturing a microbe having a polyhydroxyalkanoic acid synthase gene and an inactivated gene encoding a flagellar protein to cause the microbe to produce polyhydroxyalkanoic acid. In the microbe, a lipase, a dephosphorylating enzyme, and a protein represented by the amino acid sequence of SEQ ID NO: 6 or 7 may be additionally inactivated. The microbe may be *Cupriavidus necator*.

16 Claims, No Drawings
Specification includes a Sequence Listing.

METHOD FOR PRODUCING POLYHYDROXYALKANOIC ACID, AND MICROBES

TECHNICAL FIELD

The present invention relates to a method for producing polyhydroxyalkanoic acid with microbes and the microbes.

BACKGROUND ART

Significance and importance of production of substances by using microbes (fermentative production, bioconversion, etc.) are increasingly growing on the basis of increasing concerns for environmental issues, food issues, health and safety, as well as elevation of orientation for native or nature, and the like, and the production of substances by microbes is also applied to production of protein drugs and nucleic acids for gene therapy and the like. For example, production of ethanol, acetic acid, and proteins for pharmaceutical use, and the like utilizing microbes such as yeast and bacteria are actively and industrially applied.

One example is the production of polyhydroxyalkanoic acid (hereinafter also referred to as PHA) by a microbe, which is expected to be industrially used as a biodegradable plastic (see NPTL 1). PHA is a thermoplastic polyester produced and accumulated in cells of many microbe spices as an energy storage material, and has biodegradability. At present, more attention is being paid to non-petroleum-derived plastics due to the increasing concerns for environmental issues, and among these, in particular, PHAs produced by microbes and accumulated in their cell bodies are expected to have only a small adverse effect on the ecosystem because they can be incorporated into the natural carbon cycle process, and thus practical use of PHAs is desired. In PHA production utilizing microbes, for example, it is known that sugar, vegetable oils and fatty acids as a carbon source are given to the bacterium *Cupriavidus necator* to accumulate PHA in cells, and thus to produce PHA (See NPTL 2 and 3).

However, in production of substances by using microbes, there are cases where it becomes a problem that production cost increases due to problems such as complicated operations, medium cost, and low productivity (low product concentration and/or low production rate). Accordingly, improving the productivity in microbial culture and improving efficiency of production of substances by microbes have been major tasks for reducing production cost.

CITATION LIST

Non-Patent Literature

NPTL 1: Anderson A J., et al., Int. J. Biol. Macromol., 12, 201-105 (1990)
NPTL 2: Sato S., et al., J. Biosci. Bioeng., 120 (3), 246-251 (2015)
NPTL 3: Insomphun C., et al., Metab. Eng., 27, 38-45 (2015)

SUMMARY OF INVENTION

Technical Problem

In view of the above circumstances, it is an object of the present invention to provide a method for producing PHA by a microbe with improved productivity of PHA, and a PHA-producing microbe used for the production method.

Solution to Problem

Generally, microbes express a wide variety of genes for the purpose of adapting to the environment (temperature, pH, nutritional state, dissolved oxygen concentration, carbon source, etc.). Proteins produced by transcription and translation of genes play an important role in environmental adaptation. Production of proteins in microbes is a necessary biological phenomenon for microbial survival, growth and adaptation to the external environment, and therefore, if protein production capacity is lowered, reduction in growth of microbes and production capacity of useful substances by microbes in accordance with the lowering of the production capacity has been a naturally expected phenomenon.

According to Raberg et al. (Raberg M., et al., App. Environ. Microbiol., 74 (14), 4477-4490 (2008)), it is reported that in a strain (HF09) that has destroyed the gene rpoN encoding a transcription factor of *Cupriavidus necator*, the amount of flagella formation decreases as compared with the wild type, and the PHA content also decreases to 34% at the end of culture. Furthermore, when a ΔPHAP1 strain is cultured in a TSB medium, formation of flagella is not confirmed, and the result is shown that the PHA content markedly decreases. As described above, in the strain in which flagellum formation ability is reduced by destroying the gene rpoN encoding the transcription factor, the result is shown that PHA productivity also decreases.

However, the inventors of the present invention have surprisingly found that, in PHA-producing microbes inherently having productivity of a flagellar protein, the PHA productivity is remarkably improved in the PHA-producing microbes in which a gene encoding the flagellar protein is inactivated, and reached the present invention.

That is, the present invention is a method for producing polyhydroxyalkanoic acid, the method including a step of culturing a microbe having a polyhydroxyalkanoic acid synthase gene and an inactivated gene encoding a flagellar protein to cause the microbe to produce polyhydroxyalkanoic acid.

Preferably, the microbe further has an inactivated gene encoding at least one protein selected from the group consisting of a lipase represented by the amino acid sequence of SEQ ID NO: 2 or 3, a dephosphorylating enzyme represented by the amino acid sequence of SEQ ID NO: 4 or 5, a protein represented by the amino acid sequence of SEQ ID NO: 6 or 7, and a protein represented by the amino acid sequence having a sequence homology of 90% or more to the amino acid sequence of any one of SEQ ID NOS: 2 to 7.

Preferably, the polyhydroxyalkanoic acid is a copolymer of 3-hydroxybutyric acid and 3-hydroxyhexanoic acid.

The present invention is also a microbe having a polyhydroxyalkanoic acid synthase gene and an inactivated gene encoding a flagellar protein.

Preferably, the microbe is *Cupriavidus necator*.

Advantageous Effects of Invention

According to the present invention, when PHA is produced by microbes, the productivity of PHA can be improved. Furthermore, it is possible to reduce proteins excreted extracellularly during microbial culturing.

DESCRIPTION OF EMBODIMENTS

Hereinafter, the present invention will be described in detail.

A microbe according to the present invention is a PHA-producing microbe having a PHA synthase gene and an inactivated gene encoding a flagellar protein (hereinafter referred to as a flagella-disrupted strain of the present invention).

(Microbe)

A microbe having an inactivated gene encoding a flagellar protein according to the present invention is not particularly limited, and examples thereof include bacteria, yeasts, and filamentous fungi. The microbe is preferably a bacterium. Preferred examples of the bacteria include bacteria belonging to the genus *Ralstonia*, the genus *Cupriavidus*, the genus *Wautersia*, the genus *Aeromonas*, the genus *Escherichia*, the genus *Alcaligenes*, and the genus *Pseudomonas*. From the safety and the productivity, more preferred are bacteria belonging to the genus *Ralstonia*, the genus *Cupriavidus*, the genus *Aeromonas*, and the genus *Wautersia*, even more preferred are bacteria belonging to the genus *Cupriavidus* or the genus *Aeromonas*, and even more preferred are bacteria belonging to the genus *Cupriavidus*. Particularly preferred is *Cupriavidus necator*.

Although the flagella-disrupted strain of the present invention is a PHA-producing microbe having a PHA synthase gene, a microbe having an inactivated gene encoding a flagellar protein may be a wild strain inherently having a PHA synthase gene, a mutant strain obtained by subjecting such a wild strain to an artificial mutation process, or a bacterial strain into which a foreign PHA synthase gene is introduced by a genetic engineering procedure.

(PHA Synthase Gene)

The PHA synthase gene to be introduced by transformation is not particularly limited, and examples thereof include polyhydroxyalkanoic acid synthase genes derived from Aeromonas caviae, Aeromonas hydrophila, Pseuromonas SP 61-3, and *Cupriavidus necator*, and mutants thereof. Examples of such mutants include base sequences that encode PHA synthases modified by deletion, addition, insertion, or substitution of one or more amino acid residues. Specific examples include a gene encoding a polyhydroxyalkanoic acid synthase represented by the amino acid sequence of SEQ ID NO: 8 and a gene represented by the amino acid sequence having a sequence homology of 90% or more to the amino acid sequence of SEQ ID NO: 8 and encoding polypeptide having polyhydroxyalkanoic acid synthase activity. The above-mentioned sequence homology is preferably 95% or more, more preferably 97% or more, and particularly preferably 99% or more.

(PHA)

The type of PHA produced by the flagella-disrupted strain of the present invention is not particularly limited as long as it is PHA that can be produced by a microbe, but is preferably a homopolymer of a monomer selected from 3-hydroxyalkanoic acid having 4 to 16 carbon atoms, a copolymer of a monomer selected from 3-hydroxyalkanoic acid having 4 to 16 carbon atoms and another hydroxyalkanoic acid (e.g., 4-hydroxyalkanoic acid having 4 to 16 carbon atoms), or a copolymer of two or more monomers selected from 3-hydroxyalkanoic acid having 4 to 16 carbon atoms. Examples thereof include, but are not limited to, P(3HB) which is a homopolymer of 3-hydroxybutyric acid (abbreviation: 3HB), a copolymer P(3HB-co-3HV) of 3HB and 3-hydroxyvaleric acid (abbreviation: 3HV), a copolymer P(3HB-co-3HH) (abbreviation: PHBH) of 3HB and 3-hydroxyhexanoic acid (abbreviation: 3HH), a copolymer P(3HB-co-4HB) of 3HB and 4-hydroxybutyric acid (abbreviation: 4HB), and PHA containing lactic acid (abbreviation: LA) as a constitutive component, such as a copolymer P(LA-co-3HB) of 3HB and LA. Out of these PHAs, PHBH is preferred because of its wide application range as a polymer. The type of the PHA to be produced is appropriately selectable, depending on purpose, in accordance with the type of a PHA synthase gene included in the microbe to be used or separately introduced, the type of genes of a metabolic system related to the synthesis, the culture conditions, and others.

(Flagellar Protein)

The flagella-disrupted strain of the present invention is obtained by inactivating a gene encoding a flagellar protein inherently possessed by a microbe. The flagellar protein refers to a protein constituting flagellar fibers (flagellin). Flagella are cell organs involved in the movement of cells and include extracellularly extended flagellar proteins, hook proteins, and proteins constituting rings and rods present in a lipopolysaccharide membrane, a peptidoglycan layer, a periplasmic layer, and an adipose membrane in a cell surface membrane. In bacteria, it is known that there are bacteria having several flagella such as *Escherichia coli*, *Salmonella*, *Bacillus subtilis*, and *Cupriavidus* bacteria, and bacteria having a single flagellum such as *Vibrio* bacteria. A flagellar protein gene to be inactivated is not particularly limited as long as it is a flagellar protein gene inherently possessed by a microbe. When the microbe is *Cupriavidus necator*, the flagellar protein has the amino acid sequence of SEQ ID NO: 1. In the present invention, it is preferable that a gene encoding a flagellar protein represented by the amino acid sequence of SEQ ID NO: 1 or a gene encoding a flagellar protein represented by the amino acid sequence having a sequence homology of 90% or more to the amino acid sequence of SEQ ID NO: 1 is inactivated. The above-mentioned sequence homology is preferably 95% or more, more preferably 97% or more, and particularly preferably 99% or more.

(Inactivation)

In the present invention, examples of a method of inactivating the flagellar protein gene include a method of hampering synthesis of flagellar protein and a method for hampering transport of flagellar protein synthesized intracellularly to the outside of the cell. More specific examples thereof include a method of deleting all or part of the base sequence of a gene encoding a flagellar protein or a promoter sequence of the gene; a method of introducing a termination codon in the middle of the base sequence; a method of inhibiting transcription of the gene; and a method of stopping or suppressing the function of a system that transports flagellar proteins the outside of the cell (chaperone protein, signal sequence, transporter protein, etc.). The flagellar protein gene may be inactivated using a genetic engineering procedure, or may be inactivated using a technique of inducing a mutation.

(Other Genes to be Inactivated)

In the flagella-disrupted strain of the present invention, although marked improvement in the PHA productivity has been confirmed, it has been also confirmed that the concentration of protein accumulated extracellularly decreases during microbial culturing. Although these effects are achieved by inactivation of the flagellar protein gene, the effects can be more enhanced by inactivating other protein genes in addition to the flagellar protein gene.

In the present invention, in addition to the flagellar protein gene, the protein gene to be inactivated is not particularly limited; however, from the viewpoint of improving the PHA productivity and reducing the concentration of extracellular protein, it is preferable that the protein is an enzyme protein such as lipase including phospholipase, phosphatase including alkaline phosphatase, or a protein represented by the amino acid sequence of SEQ ID NO: 6 or 7; a protein present in the periplasmic region of the cells such as a substrate binding domain of ABC transporter (Locher K P., et al., Phil. Trans. R Soc. B, 346, 239-245 (2009)), or the like. More preferred is phospholipase, alkaline phosphatase, a protein represented by the amino acid sequence of SEQ ID NO: 6 or 7 or a homologous protein thereof, or a combination thereof. Particularly preferred is phospholipase represented by the amino acid sequence of SEQ ID NO: 2 or 3 or a homologous protein thereof, phosphatase represented by the amino acid sequence of SEQ ID NO: 4 or 5 or a homologous protein thereof, or a protein represented by the amino acid sequence of SEQ ID NO: 6 or 7 or a homologous protein thereof, or a combination thereof. Here, the homologous protein refers to a protein which is represented by the amino acid sequence having a sequence homology of 90% or more to the amino acid sequence specified above and which exhibits the enzyme activity specified above. The above-mentioned sequence homology is preferably 95% or more, more preferably 97% or more, and particularly preferably 99% or more. As a method of inactivating these other protein genes, the same method as the above-mentioned method of inactivating flagellar protein can be mentioned.

(PHA Production Method)

PHA can be accumulated in cell bodies by culturing the flagella-disrupted strain of the present invention. As a method of culturing the flagella-disrupted strain of the present invention, it is possible to use a conventional method of culturing a microbe, and the culture may performed by adding a suitable carbon source to a medium. The medium composition, an addition method of the carbon source, culture scale, conditions of ventilation and stirring, as well as culture temperature, and culture time are not particularly limited. It is preferred that the carbon source is added to the medium continuously or intermittently.

The culture is performed for a suitable period of time to accumulate PHA in the cell bodies, PHA is then recovered from the cell bodies using well-known methods. Specifically, the following method can be used. After the termination of the culture, a centrifugal separator or the like is used to separate the cell bodies from the culture solution. The cell bodies are washed with distilled water, methanol or the like, and dried. From the dried cell bodies, an organic solvent such as chloroform is used to extract the PHA. Form this PHA-containing solution, cell body components are removed by filtration or the like, and a poor solvent such as methanol or hexane is added to the filtrate to precipitate the PHA. Furthermore, filtration or centrifugal separation is used to remove the supernatant, and the remnant is then dried to collect the PHA.

According to the PHA production method using the flagella-disrupted strain of the present invention, from the viewpoint of PHA production on an industrial scale using microbes, preferably 150 g/L or more, more preferably 160 g/L or more, an still more preferably 170 g/L or more of the PHA production amount can be achieved. In addition, preferably 800 mg/L or less, more preferably 700 mg/L or less, still more preferably 500 mg/L or less, and most preferably 300 mg/L or less of the protein concentration in the culture supernatant can be achieved. A reduction in the protein concentration in the supernatant serves to provide advantages such as improvement of raw material yield and load reduction in wastewater treatment.

EXAMPLES

Hereinafter, the present invention will be described more specifically with reference to examples. However, the present invention is not limited to these examples.

(Method of Measuring PHA Production Amount)

After termination of culture, 10 ml of a culture solution was weighed, and cell bodies were collected by centrifugal separation, washed with methanol, and lyophilized. Then, the weight of the dry cell bodies was measured to obtain a dry cell body weight (X g/L).

To 1 g of the resultant dry cell bodies was added chloroform in an amount of 100 ml. At room temperature, the resultant was stirred a whole day and night. PHA in the cell bodies was extracted. The cell body residue was filtered off, and the filtrate was subjected to an evaporator to concentrate it until the total volume thereof was 30 ml. Thereto was then gradually added hexane in an amount of 90 ml. The liquid was allowed to stand still for 1 hour while slowly stirred. The precipitated PHA was filtered, and the PHA was vacuum-dried at 50° C. for 3 hours. The weight of the dried PHA was measured, and the polymer content (Y wt %) in the cell bodies was then calculated. The PHA production amount (Z g/L) was calculated by the formula of X×Y/100=Z.

(Method of Measuring Protein Concentration)

In each of examples and comparative examples, the protein concentration in a culture supernatant was measured by the following method.
(1) 1 ml of the culture solution was placed in a 1.5 ml microtube and centrifuged at 15000 g for 5 minutes.
(2) The supernatant after centrifugation was separated.
(3) The protein concentration in the separated culture supernatant was quantified with a protein assay kit (Quick Start Protein Assay manufactured by Bio-Rad Laboratories, Inc.). As a protein for preparing a calibration curve, BSA was used.

Production Example 1

Preparation of KNK-252/dfliC Strain

Initially, a plasmid for gene disruption was prepared. The preparation was performed as follows. A chromosome DNA of a C. necator H16 strain was used as a template to perform PCR, using primers represented by SEQ ID NO: 9 and SEQ ID NO: 10. PCR was performed (1) at 98° C. for 2 minutes, (2) at 98° C. for 15 seconds, (3) at 60° C. for 30 seconds, and (4) at 68° C. for 2 minutes (25 cycles) with a polymerase KOD-plus- (manufactured by Toyobo Co., Ltd.). In the same way, PCR was performed using primers represented by SEQ ID NO: 11 and SEQ ID NO: 12. In addition, the two DNA fragments yielded in the PCRs were used as a template to perform PCR under the same conditions, using primers represented by SEQ ID NOS: 9 and 12, and the resultant DNA fragment was digested with a restriction enzyme SmiI.

The DNA fragment obtained by digestion was linked to a vector pNS2X-sacB digested with SmiI and described in JP 2007-259708 A through a DNA ligase (Ligation High (manufactured by Toyobo Co., Ltd.)) to prepare a plasmid vector pNS2X-sacB+fliCUD for gene disruption having a base sequence on the upstream side of a fliC structural gene and a base sequence on the downstream side of the fliC structural gene.

Next, gene-disrupted strains were prepared. The preparation was performed as follows. The plasmid vector pNS2X-sacB+fliCUD for gene disruption was used to transform an E. coli S17-1 strain (ATCC47055), and the resultant and a KNK-005 REP-PHAJ4b ΔPHAZ1::Plac-PHACReΔPHAZ2,6 strain (see WO 2015/146195; hereafter, this bacterial strain was referred to as a KNK-252 strain)

were subjected to mixed culture on a nutrient agar medium (manufactured by Difco) to attain a conjugative transfer.

The KNK-252 strain is a bacterial strain in which the entire length of the PHAZ1 gene and that of the PHAZ6 gene on any chromosome of a *Cupriavidus necator* H16 strain are deleted, a sequence from the 16th codon of the PHAZ2 gene to the termination codon thereof is deleted, an expression regulatory sequence composed of a REP promoter and a PHAC1SD (REP-SD) sequence is inserted immediately upstream of the PHAJ4b gene, a lac promoter, a PHAC1SD (REP-SD) sequence, and a PHACRe structural gene sequence are inserted into the PHAZ1-gene-deleted region, and the chromosome has, thereon, a gene encoding a PHA synthase of SEQ ID NO: 8.

The cell bodies after the mixed culture was inoculated onto Simmons' agar medium containing 250 mg/L of kanamycin (2 g/L of sodium citrate, 5 g/L of sodium chloride, 0.2 g/L of magnesium sulfate heptahydrate, 1 g/L of ammonium dihydrogenphosphate, 1 g/L of dipotassium hydrogenphosphate, and 15 g/L of agar; pH: 6.8), and a bacterial strain which was growing on the agar medium was selected to gain a strain in which the plasmid was introduced onto the chromosome of the KNK-252 strain. This strain was subjected to two-generation culture on a nutrient broth medium (manufactured by Difco), and then diluted and applied onto a nutrient agar medium containing 15% of sucrose. In this way, the bacterial strain which was growing was gained as a plasmid-dropped-out strain.

Further, PCR analysis was performed to isolate one bacterial strain in which from the start codon to the termination codon of the fliC gene (flagellar protein gene) encoding the amino acid sequence of SEQ ID NO: 1 on the chromosome had been deleted. This gene-disrupted strain was named a KNK-252/dfliC strain.

Production Example 2

Preparation of KNK-252/dplcN4 Strain

Initially, a plasmid for gene disruption was prepared. The preparation was performed as follows. A chromosome DNA of a *C. necator* H16 strain was used as a template to perform PCR, using primers represented by SEQ ID NO: 13 and SEQ ID NO: 14 under the conditions described in Production Example 1. In the same way, PCR was performed using primers represented by SEQ ID NO: 15 and SEQ ID NO: 16. In addition, the two DNA fragments yielded in the PCRs were used as a template to perform PCR under the same conditions, using primers represented by SEQ ID NOS: 13 and 16, and the resultant DNA fragment was digested with a restriction enzyme SmiI.

The DNA fragment obtained by digestion was linked to a vector pNS2X-sacB digested with SmiI and described in JP 2007-259708 A through a DNA ligase (Ligation High (manufactured by Toyobo Co., Ltd.)) to prepare a plasmid vector pNS2X-sacB+ plcN4UD for gene disruption having a base sequence on the upstream side of a plcN4 structural gene and a base sequence on the downstream side of the plcN4 structural gene.

Next, in the same manner as in the preparation method of a gene-disrupted strain in Production Example 1, a KNK-252/dplcN4 strain as a chromosomal gene-disrupted strain in which from the start codon to the termination codon of the plcN4 gene (phospholipase gene) on the chromosome had been deleted was obtained by using the KNK-252 strain as a parent strain and the plasmid vector pNS2X-sacB+ plcN4UD for gene disruption.

Production Example 3

Preparation of KNK-252/dfliC/dplcN4 Strain

In the same manner as in the preparation method of a gene-disrupted strain in Production Example 1, a KNK-252/dfliC/dplcN4 strain as a chromosomal gene-disrupted strain in which from the start codon to the termination codon of the plcN4 gene on the chromosome had been deleted was obtained by using the KNK-252/dfliC strain prepared in Production Example 1 as a parent strain and the plasmid vector pNS2X-sacB+plcN4UD for gene disruption prepared in Production Example 2. The KNK-252/dfliC/dplcN4 strain is a strain in which from the start codon to the termination codon of the fliC gene on the chromosome of the KNK-252 strain have been deleted and from the start codon to the termination codon of the plcN4 gene have been deleted.

Production Example 4

Preparation of KNK-252/dfliC/dplcN4/dphoA1,2 Strain

Initially, a plasmid for gene disruption was prepared. A phoA1 structural gene and a phoA2 structural gene forms an operon on the genome of the *C. necator* H16 strain, and a plasmid was designed to disrupt this phoA operon. The preparation was performed as follows. A chromosome DNA of a *C. necator* H16 strain was used as a template to perform PCR, using primers represented by SEQ ID NO: 17 and SEQ ID NO: 18 under the conditions described in Production Example 1. In the same way, PCR was performed using primers represented by SEQ ID NO: 19 and SEQ ID NO: 20. In addition, the two DNA fragments yielded in the PCRs were used as a template to perform PCR under the same conditions, using primers represented by SEQ ID NOS: 17 and 20, and the resultant DNA fragment was digested with a restriction enzyme SmiI.

The DNA fragment obtained by digestion was linked to a vector pNS2X-sacB digested with SmiI and described in JP 2007-259708 A through a DNA ligase (Ligation High (manufactured by Toyobo Co., Ltd.)) to prepare a plasmid vector pNS2X-sacB+phoA1,2UD for gene disruption having a base sequence on the upstream side of the phoA operon and a base sequence on the downstream side of the phoA operon.

Next, in the same manner as in the preparation method of a gene-disrupted strain in Production Example 1, a KNK-252/dfliC/dplcN4/dphoA1,2 strain as a chromosomal gene-disrupted strain in which from the start codon of the phoA1 gene to the termination codon of the phoA2 gene (the gene encoding a dephosphorylating enzyme represented by the amino acid sequences of SEQ ID NOS: 4 and 5) on the chromosome had been deleted was obtained by using the KNK-252/dfliC/dplcN4 strain prepared in Production Example 3 as a parent strain and the plasmid vector pNS2X-sacB+phoA1,2UD for gene disruption.

Production Example 5

Preparation of KNK-252/dfliC/dplcN1,4/dphoA1,2 Strain

A chromosome DNA of a *C. necator* H16 strain was used as a template to perform PCR, using primers represented by SEQ ID NO: 21 and SEQ ID NO: 22 under the conditions described in Production Example 1. In the same way, PCR was performed using primers represented by SEQ ID NO: 23 and SEQ ID NO: 24. In addition, the two DNA fragments yielded in the PCRs were used as a template to perform PCR under the same conditions, using primers represented by SEQ ID NOS: 21 and 24, and the resultant DNA fragment was digested with a restriction enzyme SmiI.

The DNA fragment obtained by digestion was linked to a vector pNS2X-sacB digested with SmiI and described in JP 2007-259708 A through a DNA ligase (Ligation High (manufactured by Toyobo Co., Ltd.)) to prepare a plasmid vector pNS2X-sacB+plcN1UD for gene disruption having a base sequence on the upstream side of plcN1, and a base sequence on the downstream side of plcN1.

Next, in the same manner as in the preparation method of a gene-disrupted strain in Production Example 1, a KNK-252/dfliC/dplcN1,4/dphoA1,2 strain as a chromosomal gene-disrupted strain in which from the start codon to the termination codon of the plcN1 gene (phospholipase gene) on the chromosome had been deleted was obtained by using the KNK-252/dfliC/dplcN4/dphoA1,2 strain prepared in Production Example 4 as a parent strain and the plasmid vector pNS2X-sacB+plcN1UD for gene disruption.

Production Example 6

Preparation of
KNK-252/dfliC/dplcN1,4/dphoA1,2/B1168 Strain

A chromosome DNA of a *C. necator* H16 strain was used as a template to perform PCR, using primers represented by SEQ ID NO: 25 and SEQ ID NO: 26 under the conditions described in Production Example 1. In the same way, PCR was performed using primers represented by SEQ ID NO: 27 and SEQ ID NO: 28. In addition, the two DNA fragments yielded in the PCRs were used as a template to perform PCR under the same conditions, using primers represented by SEQ ID NOS: 25 and 28, and the resultant DNA fragment was digested with a restriction enzyme SmiI.

The DNA fragment obtained by digestion was linked to a vector pNS2X-sacB digested with SmiI and described in JP 2007-259708 A through a DNA ligase (Ligation High (manufactured by Toyobo Co., Ltd.)) to prepare a plasmid vector pNS2X-sacB+B1168UD for gene disruption having a base sequence on the upstream side of the gene described in SEQ ID NO: 29, and a base sequence on the downstream side of this gene.

Next, in the same manner as in the preparation method of a gene-disrupted strain in Production Example 1, a KNK-252/dfliC/dplcN1,4/dphoA1,2/B1168 strain as a chromosomal gene-disrupted strain in which from the start codon to the termination codon of the gene described in SEQ ID NO: 29 (the gene encoding protein represented by the amino acid sequence of SEQ ID NO: 7) on the chromosome had been deleted was obtained by using the KNK-252/dfliC/dplcN1,4/dphoA1,2 strain prepared in Production Example 5 as a parent strain and the plasmid vector pNS2X-sacB+B1168UD for gene disruption.

Production Example 7

Preparation of
KNK-252/dfliC/dplcN1,4/dphoA1,2/B1168/A3733
Strain

A chromosome DNA of a *C. necator* H16 strain was used as a template to perform PCR, using primers represented by SEQ ID NO: 30 and SEQ ID NO: 31 under the conditions described in Production Example 1. In the same way, PCR was performed using primers represented by SEQ ID NO: 32 and SEQ ID NO: 33. In addition, the two DNA fragments yielded in the PCRs were used as a template to perform PCR under the same conditions, using primers represented by SEQ ID NOS: 30 and 33, and the resultant DNA fragment was digested with a restriction enzyme SmiI.

The DNA fragment obtained by digestion was linked to a vector pNS2X-sacB digested with SmiI and described in JP 2007-259708 A through a DNA ligase (Ligation High (manufactured by Toyobo Co., Ltd.)) to prepare a plasmid vector pNS2X-sacB+A3733UD for gene disruption having a base sequence on the upstream side of the gene described in SEQ ID NO: 34 and a base sequence on the downstream side of this gene.

Next, in the same manner as in the preparation method of a gene-disrupted strain in Production Example 1, a KNK-252/dfliC/dplcN1,4/dphoA1,2/B1168/A3733 strain as a chromosomal gene-disrupted strain in which from the start codon to the termination codon of the gene described in SEQ ID NO: 34 (the gene encoding protein represented by the amino acid sequence of SEQ ID NO: 6) on the chromosome had been deleted was obtained by using the KNK-252/dfliC/dplcN1,4/dphoA1,2/B1168 strain prepared in Production Example 6 as a parent strain and the plasmid vector pNS2X-sacB+A3733UD for gene disruption.

Examples 1 to 6 and Comparative Examples 1 to 3

Production of PHA

Culture was studied using the microbes prepared in Production Examples 1 to 7, the *C. necator* H16 strain (ATCC 17699 strain) and the KNK-252 strain.

The composition of a seed medium was: 1 w/v % Meat-extract, 1 w/v % Bacto-Tryptone, 0.2 w/v % Yeast-extract, 0.9 w/v % $Na_2HPO_4.12H_2O$, 0.15 w/v % $KH_2PO_4$, (pH 6.8).

The composition of a preculture medium was: 1.1 w/v % $Na_2HPO_4.12H_2O$, 0.19 w/v % $KH_2PO_4$, 1.29 w/v % $(NH_4)_2SO_4$, 0.1 w/v % $MgSO_4.7H_2O$, 2.5 w/v % palm olein oil, and 0.5 v/v % trace metal salt solution (prepared by dissolving, in 0.1 N hydrochloric acid, 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$). Palm olein oil was added at one time as a carbon source at a concentration of 10 g/L.

The composition of the PHA production medium was: 0.385 w/v % $Na_2HPO_4.12H_2O$, 0.067 w/v % $KH_2PO_4$, 0.291 w/v % $(NH_4)_2SO_4$, 0.1 w/v % $MgSO_4.7H_2O$, 0.5 v/v % trace metal salt solution (prepared by dissolving, in 0.1 N hydrochloric acid, 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$).

First, a glycerol stock (50 μl) of each strain was inoculated into the seed medium (10 ml) and seed-cultured for 24 hours. Then, the resulting seed culture solution was inoculated at 1.0 v/v % into a 3-liter jar fermenter (MDL-300 manufactured by B. E. MARUBISHI Co., Ltd.) containing 1.8 L of the preculture medium. Preculture was performed for 28 hours under operation conditions where a culture temperature was 33° C., a stirring speed was 500 rpm, and a ventilation volume was 1.8 L/min while pH was controlled to be in the range of 6.7 to 6.8. The pH control was performed by using a 14% aqueous ammonium hydroxide solution.

Then, the resulting preculture solution was inoculated at 5.0 v/v % into a 5-liter jar fermenter (MDS-U50 manufactured by B. E. MARUBISHI Co., Ltd.) containing 2.5 L of the PHA production medium. Culture was performed under operation conditions where a culture temperature was 33° C., a stirring speed was 420 rpm, and a ventilation volume was 2.1 L/min while pH was controlled to be in the range of 6.7 to 6.8. The pH control was performed by using a 25% aqueous ammonium hydroxide solution. The carbon source was added intermittently. Palm olein oil was used as the carbon source. Culture was performed for 48 hours. A culture solution sample was obtained at the termination of the culture, and the PHA production amount and the protein concentration were measured by the above-mentioned method. The results are shown in Table 1.

As a result of the culture, improvement in PHA productivity was observed in the strains of Production Examples 1 and 3 to 8 in which the flagellar protein was inactivated, as compared with the strains of comparative examples in which the flagellar protein was not inactivated. In addition, in the strains of Production Examples 1 and 3 to 8, a decrease in the protein concentration in the culture supernatant was confirmed as compared with the strains of comparative examples.

It was confirmed by HPLC analysis that the polyhydroxyalkanoic acid produced by the strain of each production example was PHBH.

TABLE 1

| Strain | | PHA production amount (g/L) | Protein concentration (mg/L) |
|---|---|---|---|
| Example 1 | KNK-252/dfliC (Production Example 1) | 181 | 691 |
| Example 2 | KNK-252/dfliC/dplcN4 (Production Example 3) | 175 | 503 |
| Example 3 | KNK-252/dfliC/dplcN4/dphoA1, 2 (Production Example 4) | 175 | 461 |
| Example 4 | KNK-252/dfliC/dplcN1, 4/dphoA1, 2 (Production Example 5) | 179 | 390 |
| Example 5 | KNK-252/dfliC/dplcN1, 4/dphoA1, 2/B1168 (Production Example 6) | 180 | 378 |
| Example 6 | KNK-252/dfliC/dplcN1, 4/dphoA1, 2/B1168/A3733 (Production Example 7) | 183 | 330 |
| Comparative Example 1 | KNK-252 | 155 | 896 |
| Comparative Example 2 | C. necator H16 | 150 | 904 |
| Comparative Example 3 | KNK-252/dplcN4 (Production Example 2) | 155 | 774 |

---

The invention claimed is:

1. A method for producing polyhydroxyalkanoic acid, the method comprising:
   culturing a microbe comprising a polyhydroxyalkanoic acid synthase gene and an inactivated gene encoding a flagellar protein to cause the microbe to produce polyhydroxyalkanoic acid,
   wherein the microbe belongs to the genus *Cupriavidus*, and
   wherein the polyhydroxyalkanoic acid synthase gene encodes a polyhydroxyalkanoic acid synthase comprising an amino acid sequence having a sequence homology of 90% or more to the amino acid sequence of SEQ ID NO: 8.

2. The method according to claim 1, wherein the microbe further comprises an inactivated gene encoding at least one protein selected from the group consisting of a lipase comprising the amino acid sequence of SEQ ID NO: 2 or 3, a dephosphorylating enzyme comprising the amino acid sequence of SEQ ID NO: 4 or 5, a protein comprising the amino acid sequence of SEQ ID NO: 6 or 7, and a protein comprising an amino acid sequence having a sequence homology of 90% or more to the amino acid sequence of SEQ ID NO: 2, 3, 4, 5, 6, or 7.

3. A method for producing polyhydroxyalkanoic acid, the method comprising:
   culturing a microbe comprising a polyhydroxyalkanoic acid synthase gene and an inactivated gene encoding a flagellar protein to cause the microbe to produce polyhydroxyalkanoic acid,
   wherein the microbe belongs to the genus *Cupriavidus*, and
   wherein the polyhydroxyalkanoic acid is a copolymer of 3-hydroxybutyric acid and 3-hydroxyhexanoic acid.

4. A microbe comprising a polyhydroxyalkanoic acid synthase gene and an inactivated gene encoding a flagellar protein, wherein the microbe belongs to the genus *Cupriavidus*,
   wherein the polyhydroxyalkanoic acid synthase gene encodes a polyhydroxyalkanoic acid synthase comprising an amino acid sequence having a sequence homology of 90% or more to the amino acid sequence of SEQ ID NO: 8.

5. The microbe according to claim 4, wherein the microbe is *Cupriavidus necator*.

6. The method according to claim 2, wherein the polyhydroxyalkanoic acid is a copolymer of 3-hydroxybutyric acid and 3-hydroxyhexanoic acid.

7. The method according to claim 1, wherein the microbe is *Cupriavidus necator*.

8. The method according to claim 1, wherein the polyhydroxyalkanoic acid synthase gene encodes a polyhydroxyalkanoic acid synthase comprising an amino acid sequence having a sequence homology of 95% or more to the amino acid sequence of SEQ ID NO: 8.

9. The method according to claim 1, wherein the flagellar protein comprises an amino acid sequence having a sequence homology of 90% or more to the amino acid sequence of SEQ ID NO: 1.

10. The method according to claim 1, wherein the flagellar protein comprises an amino acid sequence having a sequence homology of 95% or more to the amino acid sequence of SEQ ID NO: 1.

11. The method according to claim 1, further comprising: collecting the produced polyhydroxyalkanoic acid.

12. The method according to claim 1, wherein the culturing is performed in a medium while adding a carbon source to the medium.

13. The microbe according to claim 4, wherein the polyhydroxyalkanoic acid synthase gene encodes a polyhydroxyalkanoic acid synthase comprising an amino acid sequence having a sequence homology of 95% or more to the amino acid sequence of SEQ ID NO: 8.

14. The microbe according to claim 4, wherein the flagellar protein comprises an amino acid sequence having a sequence homology of 90% or more to the amino acid sequence of SEQ ID NO: 1.

15. The microbe according to claim 4, wherein the flagellar protein comprises an amino acid sequence having a sequence homology of 95% or more to the amino acid sequence of SEQ ID NO: 1.

16. The method according to claim 1, wherein the polyhydroxyalkanoic acid is a copolymer of 3-hydroxybutyric acid and 3-hydroxyhexanoic acid.

* * * * *

SEQUENCE LISTING

<160> NUMBER OF SEQ ID NOS: 34

<210> SEQ ID NO 1
<211> LENGTH: 435
<212> TYPE: PRT
<213> ORGANISM: Cupriavidus necator H16

<400> SEQUENCE: 1

Met Ala Gln Val Ile Asn Thr Asn Ser Leu Ser Leu Met Thr Gln Asn
1               5                   10                  15

Asn Met Asn Thr Ser Gln Ser Ser Leu Asn Thr Ala Ile Gln Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Arg Gly Leu Thr Gln Ala
    50                  55                  60

Gln Arg Asn Ala Asn Asp Gly Ile Ser Leu Ala Gln Thr Thr Glu Gly
65                  70                  75                  80

Ala Leu Thr Glu Val Asn Asn Asn Leu Gln Arg Ile Arg Glu Leu Ser
                85                  90                  95

Val Gln Ala Ala Thr Gly Ser Asn Ser Ser Ser Asp Leu Lys Ser Ile
            100                 105                 110

Gln Asp Glu Ile Asn Gln Arg Leu Ser Glu Ile Asp Arg Thr Ser Gln
        115                 120                 125

Gln Thr Asp Phe Asn Gly Val Lys Val Leu Ala Gly Ser Asn Lys Leu
    130                 135                 140

Ser Val Gln Val Gly Ala Asn Asp Gly Glu Thr Ile Ser Ile Asp Leu
145                 150                 155                 160

Lys Gln Ile Asp Arg Thr Thr Leu Gly Leu Ser Gly Phe Ser Val Ala
                165                 170                 175

Lys Asn Ser Leu Asp Val Gly Pro Lys Ile Thr Thr Ile Asn Ala Ala
            180                 185                 190

```
Ala Gly Thr Gly Ser Phe Asn Val Ser Phe Ala Ala Gly Asp Val Thr
            195                 200                 205

Lys Ile Asn Ala Ala Thr Gly Lys Thr Phe Ala Ala Asp Leu Glu
        210                 215                 220

Leu His Glu Val Lys Thr Ala Ala Gly Ala Asn Ser Gly Gln Phe Val
225                 230                 235                 240

Val Lys Ala Gly Asp Asp Tyr Phe Ala Ala Ser Val Asp Arg Ala Thr
                245                 250                 255

Gly Ala Val Lys Leu Asn Glu Ala Asp Val Ala Phe Asp Asp Thr Ala
            260                 265                 270

Asn Gly Ile Ala Gly Pro Val Thr Leu Gln Asp Gln Val Val Arg Val
        275                 280                 285

Ala Asn Asp Ala Ala Gly Val Ala Thr Gly Tyr Val Thr Val Gln Gly
290                 295                 300

Lys Asn Tyr Val Ala Ala Gly Thr Leu Ala Asp Gly Ala Ala Gly
305                 310                 315                 320

Thr Leu Asn Val Ala Val Gly Thr Ile Ser Leu Ser Gly Ala Thr Pro
                325                 330                 335

Thr Ala Glu Phe Thr Gly Val Pro Thr Gly Asn Ala Leu Lys Lys Ile
            340                 345                 350

Asp Ala Ala Leu Lys Gln Val Asp Asp Leu Arg Ser Ser Leu Gly Ala
        355                 360                 365

Val Gln Asn Arg Phe Asp Ser Val Ile Ser Asn Leu Gly Thr Thr Val
370                 375                 380

Thr Asn Leu Ser Ser Ser Arg Ser Arg Ile Gln Asp Ala Asp Tyr Ala
385                 390                 395                 400

Thr Glu Val Ser Asn Met Thr Arg Ala Asn Ile Leu Gln Gln Ala Gly
                405                 410                 415

Thr Ser Val Leu Ala Gln Ala Asn Gln Thr Thr Gln Gly Val Leu Ser
            420                 425                 430

Leu Leu Arg
        435

<210> SEQ ID NO 2
<211> LENGTH: 682
<212> TYPE: PRT
<213> ORGANISM: Cupriavidus necator H16

<400> SEQUENCE: 2

Pro Ala Asn Asn Ala Thr Gly Thr Ile Arg Asp Val Glu His Val Val
1               5                   10                  15

Ile Leu Met Gln Glu Asn Arg Ser Phe Asp Asn Tyr Phe Gly Thr Leu
            20                  25                  30

Arg Gly Val Arg Gly Phe Gly Asp Arg Phe Pro Ile Pro Leu Ala Gly
        35                  40                  45

Gly Leu Asn Val Trp Gln Gln Thr Tyr Thr Asn Gly Ser Thr Thr Arg
    50                  55                  60

Thr Val Leu Pro Tyr His Leu Asp Ser Ser Ala Gly Asn Ala Gln Arg
65                  70                  75                  80

Val Ser Gly Thr Pro His Ser Tyr Pro Asp Ala Gln Asn Ala Trp Asp
                85                  90                  95

Leu Gly Arg Met Asn Lys Trp Pro Thr Tyr Lys Gln Thr Gln Ser Met
            100                 105                 110

Gly Tyr Tyr Thr Glu Ala Glu Leu Asp Phe Gln Val Ala Leu Ala Asn
```

-continued

```
            115                 120                 125
Ala Phe Thr Val Cys Asp Ala Tyr His Cys Ser Phe His Gly Gly Thr
130                 135                 140
Asn Ser Asn Arg Leu Phe His Trp Thr Gly Thr Asn Asp Pro Gly Gly
145                 150                 155                 160
Ala Asn Gly Gly Pro Val Ile Asp Asn Ser Gly Asp Ser Phe Thr Gly
                165                 170                 175
Ser Ala Pro Ala Tyr Thr Trp Lys Thr Tyr Pro Glu Arg Leu Glu Ala
            180                 185                 190
Ala Gly Val Ser Trp Lys Val Tyr Gln Asn Met Pro Asp Asn Phe Thr
        195                 200                 205
Asp Asn Pro Leu Ala Gly Phe Lys Gln Tyr Arg Asp Ala Asn Ala Ala
210                 215                 220
Arg Gly Asn Gln Ala Asn Gly Ser Pro Tyr Pro Ala Tyr Thr Ser Ala
225                 230                 235                 240
Asp Asp Ala Ile Ser Pro Leu Leu Lys Gly Val Ala Asn Thr Met Pro
                245                 250                 255
Asp Gly Gly Phe Leu Gln Ser Leu Arg Asp Asp Val Ala Ala Gly Lys
            260                 265                 270
Leu Pro Gln Val Ser Trp Ile Val Ala Pro Ala Thr Tyr Ser Glu His
        275                 280                 285
Pro Gly Pro Ser Ser Pro Val Gln Gly Ala Trp Tyr Thr Gln Glu Val
290                 295                 300
Leu Asn Ala Leu Thr Ala Asn Pro Ala Val Trp Ser Lys Thr Val Leu
305                 310                 315                 320
Leu Ile Asn Phe Asp Glu Asn Asp Gly Tyr Phe Asp His Val Pro Pro
                325                 330                 335
Pro Cys Ala Pro Ala Tyr Asp Gly Asp Thr Leu Ala Gly Ala Thr Thr
            340                 345                 350
Leu Asp Pro Gln Gln Val Arg Pro Glu Tyr His Val Asp Lys Arg Pro
        355                 360                 365
Tyr Gly Pro Gly Pro Arg Val Pro Met Tyr Val Val Ser Pro Trp Ser
370                 375                 380
Arg Gly Gly Trp Val Asn Ser Gln Val Ser Asp His Thr Ser Val Leu
385                 390                 395                 400
Arg Phe Leu Glu Ala Arg Phe Gly Val Ala Glu Thr Asn Ile Ser Ser
                405                 410                 415
Phe Arg Arg Ala Val Ala Gly Asp Leu Thr Ser Ala Phe Asn Phe Val
            420                 425                 430
Ser Pro Asn Thr Asn Pro Leu Pro Thr Leu Pro Asn Arg Asp Lys Ala
        435                 440                 445
Ser Ala Asp Ala Ile Arg Thr Ala Gln Gly Val Leu Pro Gln Val Pro
450                 455                 460
Leu Pro Ser Ala Ser Gln Gln Met Pro Gln Gln Asp Thr Gly Thr
465                 470                 475                 480
Arg Pro Ser Arg Ala Leu Pro Tyr Glu Leu His Val Ser Ala Arg Glu
                485                 490                 495
Asp Ala Arg Asp Gln Arg Ala Val Trp Leu Leu Phe Ser Asn Thr Gly
            500                 505                 510
Thr Ala Ala Ala Val Phe His Val Tyr Asp Arg Leu His Leu Asp Arg
        515                 520                 525
Val Pro Arg Arg Tyr Met Val Glu Pro Gly Lys Glu Leu His Gly Ser
530                 535                 540
```

```
Trp Asp Val Phe Ala Ser Asp Gly Lys Tyr Asp Leu Trp Val Leu
545                 550                 555                 560

Gly Pro Asn Gly Phe His Arg Ala Phe Arg Gly Asn Val Gly Ala Val
                565                 570                 575

Thr Ala Ala Gly Ala Ser Ala Pro Glu Ile Arg Val Cys Tyr Asp Ile
            580                 585                 590

Ala Asn Ala Ala Val Tyr Val Asp Met Ile Asn Thr Gly Ser Ala Pro
        595                 600                 605

Cys Thr Phe Thr Val Gln Pro Asn Ala Tyr Arg Thr Asp Gly Pro Trp
    610                 615                 620

Thr Tyr Glu Val Pro Ala Gly Met Gln Leu Gln His Trp Pro Val
625                 630                 635                 640

Ala Arg Gln Gly Asn Trp Tyr Asp Phe Thr Val Thr Ala Gln Gly
                645                 650                 655

Gly Phe Thr Arg Arg Phe Ala Gly Arg Ile Glu Thr Gly Lys Asp Ser
                660                 665                 670

Val Ser Asp Pro Ala Met Gly Leu Asn Gly
            675                 680
```

<210> SEQ ID NO 3
<211> LENGTH: 715
<212> TYPE: PRT
<213> ORGANISM: Cupriavidus necator H16

<400> SEQUENCE: 3

```
Ile Pro Ala Asn Asn Ala Thr Gly Thr Ile Lys Asp Val Glu His Val
1               5                   10                  15

Val Ile Leu Met Gln Glu Asn Arg Ser Phe Asp His Tyr Phe Gly Thr
            20                  25                  30

Leu Lys Gly Val Arg Gly Phe Gly Asp Arg Phe Thr Ile Pro Leu Pro
        35                  40                  45

Asn Ala Arg Lys Val Trp Gln Gln Gln Arg Ser Asn Gly Ala Val Leu
    50                  55                  60

Thr Pro Tyr His Leu Asp Gly Thr Asn Asn Ala Gln Arg Ala Ala
65                  70                  75                  80

Gly Thr Pro His Ala Trp Val Asp Ser Gln Gln Ala Trp Asp His Gly
                85                  90                  95

Arg Met Ala Ser Trp Pro Thr Tyr Lys Thr Asn Thr Ser Met Gly Tyr
            100                 105                 110

Phe Lys Glu Lys Glu Ile Pro Phe Gln Phe Ala Leu Ala Asn Ala Phe
        115                 120                 125

Thr Leu Cys Asp Ala Tyr His Cys Ser Met His Thr Gly Thr Asp Ala
    130                 135                 140

Asn Arg Ser Phe His Leu Thr Gly Thr Asn Gly Pro Thr Ala Ala Asn
145                 150                 155                 160

Val Ala Phe Val Asn Asn Glu Trp Asp Ala Ile Asp Gly Leu Pro Ala
                165                 170                 175

Ser Ala Asn Thr Gly Tyr Thr Trp Lys Thr Tyr Ala Glu Arg Leu Glu
            180                 185                 190

Ala Ala Gly Ile Ser Trp Ile Cys Tyr Gln Asn Met Pro Asp Glu Trp
        195                 200                 205

Gly Asp Asn Met Leu Gly Ala Phe Gln Gln Phe Arg Lys Ala Asn Leu
    210                 215                 220

Ala Ser Gly Phe Pro Val Ser Ser Gly Gly Ala Pro Gly Ala Pro Tyr
```

```
            225                 230                 235                 240
        Ala Asn Thr Gly Gln Pro Leu Pro Tyr His Ala Tyr Asp Ala Ala Thr
                        245                 250                 255

Asp Asn Ala Ala Asn Pro Leu Tyr Lys Gly Val Ala Asn Thr Leu Pro
                        260                 265                 270

Gly Thr Arg Pro Glu Glu Tyr Leu Asp Ala Phe Arg Asp Ile Lys
                        275                 280                 285

Glu Gly Arg Leu Pro Gln Val Ser Trp Ile Asn Ala Pro Ser Ile Tyr
                        290                 295                 300

Cys Glu His Pro Gly Pro Ser Ser Pro Val Gln Gly Ala Trp Phe Leu
        305                 310                 315                 320

Gln Glu Val Leu Asp Ala Leu Thr Ala Val Pro Glu Val Trp Ser Lys
                        325                 330                 335

Thr Val Leu Leu Val Asn Phe Asp Glu Asn Asp Gly Tyr Phe Asp His
                        340                 345                 350

Val Pro Ser Pro Ser Ala Pro Ser Val Asn Pro Asp Lys Thr Leu Ala
                        355                 360                 365

Gly Lys Ala Thr Leu Ser Asp Ala Glu Met Gln Ala Glu Tyr Phe Asn
                        370                 375                 380

His Pro Pro Pro Gly Ser Arg Thr Gln Pro Ala Ala Asp Gly Arg
        385                 390                 395                 400

Val Tyr Gly Pro Gly Pro Arg Val Pro Leu Tyr Ala Ile Ser Pro Trp
                        405                 410                 415

Ser Arg Gly Gly Trp Ile Asn Ser Gln Val Phe Asp His Thr Ser Val
                        420                 425                 430

Leu Arg Phe Leu Glu Ala Arg Phe Gly Val Ala Glu Pro Asn Ile Ser
                        435                 440                 445

Pro Phe Arg Arg Ala Val Cys Gly Asp Leu Thr Ser Ala Phe Asn Phe
                        450                 455                 460

Lys Thr Pro Asn Ser Glu Ala Leu Pro Thr Leu Ser Gly Arg Thr Thr
        465                 470                 475                 480

Arg Ser Gly Ala Asp Gln Leu Arg Gln Ala Gln Ala Leu Pro Ala
                        485                 490                 495

Val Pro Leu Pro Val Asp Met Gln Leu Pro Leu Gln Ala Thr Gly Thr
                        500                 505                 510

Arg Pro Ser Arg Ala Leu Pro Tyr Glu Leu His Thr Ser Ala Arg Cys
                        515                 520                 525

Ser Ala Val Gly Gln Val Glu Leu Val Phe Ala Asn Thr Gly Thr Gln
                        530                 535                 540

Ala Ala Val Phe His Val Tyr Asp Arg Tyr Gln Leu Gly Arg Ile Pro
        545                 550                 555                 560

Arg Arg Tyr Val Val Glu Ala Arg Lys Ser Leu Ser Asp Thr Trp Asn
                        565                 570                 575

Val Phe Gln Asp Asn Ala Gly Gln Tyr Asp Leu Trp Val Leu Gly Pro
                        580                 585                 590

Asn Gly Phe His Arg His Phe Arg Gly Asp Thr Asn Arg Ile Gly Asp
                        595                 600                 605

Thr Gly Ile Ala Pro Glu Ile Arg Val Cys Tyr Asp Ile Ala Asn Gly
                        610                 615                 620

Asp Val Tyr Val Asp Leu Ile Asn Ala Gly Arg Lys Ala Cys His Phe
        625                 630                 635                 640

Ser Ile Gln Ala Leu Ala Tyr Arg Thr Asp Gly Pro Trp Pro Val Thr
                        645                 650                 655
```

```
Val Gly Ala Asn Asp Ser Lys Ser Val His Trp Ser Leu Glu Glu Ser
            660                 665                 670

Gly Gln Trp Tyr Asp Phe Ala Val Thr Cys Asp Ser Asp Pro Ala Phe
        675                 680                 685

Tyr Arg Arg Phe Ala Gly Arg Val Glu Asn Gly Arg His Thr Val Ser
    690                 695                 700

Asp Pro Ala Met Gly Met Val Thr Ala Gln Asp
705                 710                 715

<210> SEQ ID NO 4
<211> LENGTH: 446
<212> TYPE: PRT
<213> ORGANISM: Cupriavidus necator H16

<400> SEQUENCE: 4

Thr Ala Pro Ala Lys Asn Val Val Phe Phe Leu Gly Asp Gly Met Gly
1               5                   10                  15

Met Thr Thr Met Thr Ala Ala Arg Ile Tyr Lys Val Gly Glu Asp Gly
            20                  25                  30

Asp Leu Thr Met Asp Thr Leu Pro Glu Ser Gly Phe Ile Arg Thr Tyr
        35                  40                  45

Ser Asn Asn Ala Gln Val Thr Asp Ser Ala Pro Ser Met Ala Ala Tyr
    50                  55                  60

Met Thr Gly Val Lys Met Asn Asn Glu Val Ile Ser Met Thr Pro Glu
65                  70                  75                  80

Thr Asn Ala Phe Asp Ala Ser Gly Lys Asp Tyr Leu Ser Gly Ala Asp
                85                  90                  95

Ser Thr Cys Pro Ala Ser Gly Asn Gly Gln Ser Val Pro Thr Leu Leu
            100                 105                 110

Glu Gln Met Lys Ala Ala Gly Tyr Gly Thr Gly Val Val Thr Thr Thr
        115                 120                 125

Arg Ile Thr His Ala Thr Pro Ala Thr Thr Tyr Ala His Val Cys His
    130                 135                 140

Arg Asp Ala Glu Asn Thr Ile Ala Ala Gln Leu Val Pro His Gly Ala
145                 150                 155                 160

Gly Tyr Asn Ser Ala Leu Gly Asp Gly Val Asp Val Ile Phe Gly Gly
                165                 170                 175

Gly Arg Lys His Phe Gln Asn Lys Ala Ala Gly Ala Arg Thr Asp
        180                 185                 190

Gly Arg Asp Leu Val Gly Glu Leu Thr Lys Ala Gly Tyr Ala Tyr Val
    195                 200                 205

Ser Ser Lys Ala Glu Phe Asp Lys Ile Asp Ala Ala Ser Ala Lys Lys
    210                 215                 220

Val Ala Gly Leu Phe Thr Ser Ser His Met Ala Tyr Asp Leu Asp Arg
225                 230                 235                 240

Val Pro Gly Asp Glu Pro Ser Leu Ala Glu Met Thr Gly Lys Ala Ile
                245                 250                 255

Asp Val Leu Ala Ala Lys Arg Lys Gly Phe Phe Leu Met Val Glu Gly
            260                 265                 270

Gly Arg Ile Asp His Ala Leu His Glu Thr Thr Ala Arg Lys Ala Leu
        275                 280                 285

Gln Asp Thr Val Ala Phe Asp Thr Ala Ile Lys Thr Ala Ile Asp Lys
    290                 295                 300

Leu Asn Val Ile Asp Pro Gly Leu Lys Asn Thr Leu Ile Val Val Thr
```

```
            305                 310                 315                 320
Ala Asp His Asp His Thr Leu Val Leu Asn Gly Tyr Ala Lys Arg Thr
                    325                 330                 335

Gly Pro Thr Ser Asp Ser Asn Pro Gly Val Leu Gly Leu Leu Lys Asn
                    340                 345                 350

Tyr Val Thr Gly Ala Leu Ser Thr Asp Ser Gly Gly Asn Pro Phe Thr
                    355                 360                 365

Ile Ile Gly Phe Gly Thr Gly Glu Asn Arg Pro Ala Thr Arg Thr Ala
            370                 375                 380

Leu Thr Asp Ala Gln Val Tyr Asp Lys Ser Tyr His Gln Glu Ala Ala
385                 390                 395                 400

Ile Pro Thr Ala Ala Gly Gly Glu Thr His Gly Gly Thr Asp Val Phe
                    405                 410                 415

Ile Gly Ala Leu Gly Asn Gly Ala Glu Ser Phe Ala Gly Val Met Asp
                    420                 425                 430

Asn Thr Asp Val Phe Gly Leu Ile Lys Thr Ala Ile Gly Leu
                435                 440                 445

<210> SEQ ID NO 5
<211> LENGTH: 437
<212> TYPE: PRT
<213> ORGANISM: Cupriavidus necator H16

<400> SEQUENCE: 5

Ala Gly Glu Ala Lys Asn Val Ile Phe Phe Leu Gly Asp Gly Met Gly
1               5                   10                  15

Pro Thr Thr Val Thr Ala Ser Arg Ile Tyr Lys Tyr Gly Glu Thr Gly
                20                  25                  30

Lys Leu Asn Met Glu Ser Leu Lys Arg Thr Ala Arg Val Lys Thr Tyr
            35                  40                  45

Ser Asn Asp Ala Gln Thr Thr Asp Ser Ala Pro Ser Met Ala Ala Tyr
        50                  55                  60

Met Thr Gly Val Lys Met Asn Asn Glu Val Ile Ser Met Ser Ala Asp
65                  70                  75                  80

Thr Lys Ala Ser Asp Gly Thr Gly Lys Ala Tyr Val Thr Ser Ala Gly
                85                  90                  95

Asp Ser Thr Cys Pro Ser Gly Asn Gly Ala Pro Val Val Thr Val Leu
                100                 105                 110

Glu Leu Ala Lys Ala Ala Gly Lys Ser Val Gly Ala Val Thr Thr Thr
            115                 120                 125

Arg Val Thr His Ala Thr Pro Ala Ala Thr Phe Ser His Val Cys His
        130                 135                 140

Arg Asp Gly Glu Asn Asn Ile Ala Ala Gln Ala Thr Pro Gly Asn Ala
145                 150                 155                 160

Gly Tyr Asn Thr Ala Leu Lys Asp Gly Leu Asp Val Leu Leu Gly Gly
                165                 170                 175

Gly Arg Arg Gln Phe Leu Pro Asp Ser Val Thr Gly Gly Lys Arg Thr
            180                 185                 190

Asp Gly Val Asp Leu Thr Thr Gln Phe Pro Gly Tyr Thr Tyr Val Thr
        195                 200                 205

Thr Gly Thr Ala Phe Lys Ala Val Asp Pro Ala Ser Thr Ser Lys Leu
    210                 215                 220

Leu Gly Leu Phe Asn Met Asp His Leu Asn Tyr Glu Leu Asp Arg Val
225                 230                 235                 240
```

```
Lys Asn Asn Val Asp Glu Pro Ser Leu Ala Asp Met Thr Glu Lys Ala
                245                 250                 255

Ile Arg Ile Leu Gln Lys Asn Gly Asn Gly Tyr Phe Leu Met Val Glu
            260                 265                 270

Gly Gly Arg Ile Asp His Ala Leu His Gly Thr Asn Ala Lys Arg Ala
            275                 280                 285

Leu Glu Asp Thr Ile Ala Phe Asp Asp Ala Ile Lys Arg Ala Leu Ser
        290                 295                 300

Met Val Asp Leu Ser Asn Thr Met Ile Val Thr Ala Asp His Asp
305                 310                 315                 320

His Thr Met Thr Ile Asn Gly Tyr Ser His Arg Gly Asn Pro Ile Leu
                325                 330                 335

Gly Thr Ala Thr Asp Ile Lys Thr Arg Gln Pro Ala Thr Ala Ala Asp
            340                 345                 350

Gly Leu Pro Tyr Thr Thr Leu Val Phe Gly Asn Gly Gly Pro Arg
        355                 360                 365

Lys Thr Pro Arg Asp Asn Pro Ala Leu Val Asp Thr Thr Ala Asp Gly
    370                 375                 380

Tyr Leu Gln Glu Val Gly Val Asn Leu Gly Ser Pro Gly Ser Glu Thr
385                 390                 395                 400

His Gly Gly Asp Val Met Leu Phe Ser Thr Gly Pro Gly Asn Ala
                405                 410                 415

Ala Leu Lys Gly Thr Ile Asp Asn Thr Lys Val Phe Ser Val Val Lys
            420                 425                 430

Ser Ala Leu Gly Leu
            435

<210> SEQ ID NO 6
<211> LENGTH: 386
<212> TYPE: PRT
<213> ORGANISM: Cupriavidus necator H16

<400> SEQUENCE: 6

Ala Pro Ser Thr Pro Ala Ala Val Gln Thr Arg Leu Cys Pro Ala Ala
1               5                   10                  15

Leu Asp Tyr Ser Thr Thr Phe Thr Gly Gly Thr Gly Ser Gly Glu Leu
            20                  25                  30

Val Lys Val Gln Ile Asp Thr Thr Lys Lys Thr Trp Gln Val Thr Phe
        35                  40                  45

Val Asp Ser Ser Val Pro Arg Gln Thr Gly Thr Val Gln Pro Thr Arg
    50                  55                  60

Ser Asp Pro Thr Asn Gly Gln Asn Val Met Arg Gly Thr Leu Lys Ala
65                  70                  75                  80

Glu Thr Gly Leu Pro Thr Glu Lys Leu Asn Gln Cys Ala Phe Glu Leu
                85                  90                  95

Ser Gly Ala Ser Leu Asp Pro Asn Arg Pro Ala Lys Leu Phe Val Gly
            100                 105                 110

Glu Gly Val Val Gly Gly Thr Ile Pro Gly Ala Arg Ile Gln Phe Asn
        115                 120                 125

Gly Val Leu Gly Ala Gly Ala Val Pro Asp Thr Thr Phe Pro Tyr Phe
    130                 135                 140

Gln Phe Ile Gly Phe Ala Gln Thr Glu Thr Asp Leu Ser Lys Ile Ala
145                 150                 155                 160

Gly Gln Tyr Asn Gly Thr Gly Phe His Glu Val Pro Ser Lys Gln Phe
                165                 170                 175
```

```
Gln Leu Val Ala Gln Asp Tyr Arg Met Ala Leu Ala Ala Asp Gly Ser
            180                 185                 190

Phe Thr Val Cys Asp Asn Ala Thr Asn Thr Cys Glu Arg Lys Gly Asn
            195                 200                 205

Asn Phe Val Pro Gln Ala Ser Gly Ala Leu Leu Ser Thr Asn Tyr Lys
210                 215                 220

Ala Glu Ser Gln Pro Pro Thr Leu Gly Gly Thr Leu Gly Lys Ala Tyr
225                 230                 235                 240

Leu Ile Val Gly Lys Leu Arg Gly Gln Leu Val Pro Val Met Ile Arg
            245                 250                 255

Val Gly Tyr Ala Asn Asp Ser Leu Ala Asn Gly Pro Leu Gly Ala Asp
            260                 265                 270

Asp Glu Ile Gly Ile Gly Met Met Ala Pro Ala Val Ala Leu Thr Glu
            275                 280                 285

Gly Thr Val Asn Gly Glu Tyr Val Gly Val Asp Ser Asn Phe Asn Tyr
            290                 295                 300

Arg Val Thr Ala Leu Val Gly Ala Ala Ala Thr Met Met Asp Pro Phe
305                 310                 315                 320

Arg Pro His Asp Ala Ser Leu Ala Ile Pro Tyr Arg Leu Asp Phe Ser
            325                 330                 335

Gln Gln Val Pro Gly Val Val Arg Thr Ser Arg Arg Asp Ala Pro Ala
            340                 345                 350

Gly Ser Ala Pro Thr Gly Lys Leu Met Phe Thr Gly Gly Val Phe Gly
            355                 360                 365

Phe Leu Glu Gln Arg Asp Ser Gly Pro Tyr Phe Thr Val Gly Ala Phe
370                 375                 380

Val Gln
385

<210> SEQ ID NO 7
<211> LENGTH: 637
<212> TYPE: PRT
<213> ORGANISM: Cupriavidus necator H16

<400> SEQUENCE: 7

Asp Thr Thr Ile Lys Thr Pro Pro Ala Gly Ala Gly Gly Pro Arg
1               5                   10                  15

Val Leu Leu Val Gly Val Asp Gly Ala Thr Tyr Ala Gln Val Gln Gly
                20                  25                  30

Ala Leu Leu Arg Arg Glu Leu Pro Asn Leu Ala Arg Leu Asn Leu Val
            35                  40                  45

Pro Thr Ala Thr Gly Gly Met Pro Gly Thr Ile Thr Ala Gln Pro Pro
50                  55                  60

Leu Asp Ala Pro Ser Trp Ala Thr Val Leu Thr Gly Ala Trp Ala Asn
65                  70                  75                  80

Arg His Gly Ile Glu Asp Asp Thr Gly Ser Thr Ala Leu Gln Ala Pro
                85                  90                  95

Thr Val Phe Arg Tyr Leu Arg Ala Ala Gly Lys Pro Gly Leu Gln Gln
            100                 105                 110

Gly Ala Ser Thr Ser Ser Gly Val Leu Pro Gly Leu Leu Lys Ala Glu
            115                 120                 125

Gln Glu Ala Gly Met Leu Asp Thr Leu Val Asp Cys Ala Gly Val Asp
130                 135                 140

Ser Cys Val Thr Gln Asn Ala Val Arg Gln Val Gln Ser Gly Tyr Gly
```

```
            145                 150                 155                 160
Val Val Phe Ala Gln Tyr Ser Ala Pro Ala Gln Ala Glu Ala Gly
                165                 170                 175
Gly Phe Gly Asn Gly Ala Tyr Ala Thr Ala Leu Ala Gly Ile Asp Lys
                180                 185                 190
Ala Leu Gly Glu Leu Leu Gly Ala Val Ala Ala Arg Ser Gln Gly Gln
                195                 200                 205
Pro Gly Glu Asp Trp Leu Val Met Val Thr Thr Ser His Gly Leu Asp
    210                  215                 220
Ala Thr Gly Ala Thr Thr Thr Val Pro Thr Val Glu Asn Arg Thr Ala
225                  230                 235                 240
Phe Leu Ala Thr Asn Lys Ala Leu Asn Gly Ala Leu Ala Lys Pro Gly
                245                 250                 255
Ala Ala Ala Pro Asp Thr Pro Ala Asp Leu Ser Ala Leu Pro Thr Glu
                260                 265                 270
Ala Asp Leu Val Pro Thr Val Leu Ala His Ala Gly Val Ala Leu Asp
                275                 280                 285
Pro Ala Thr Thr Arg Leu Asp Gly Ser Ala Leu Thr Thr Ala Asn Ala
    290                  295                 300
Gly Val Arg Ala Ile Gly Ala Ser Ile Ser Gln Tyr Asn Asp Ala Ile
305                  310                 315                 320
Thr Leu Ser Trp Gln Asn Pro Thr Glu Ala Phe Gly Val Thr Arg Val
                325                 330                 335
Leu Arg Asp Gly Val Gln Ile Ala Ser Leu Gly Pro Glu Val Arg Gln
                340                 345                 350
Phe Thr Asp Lys Ala Phe Asn Met Ala Thr Gly Leu Tyr Gln Phe Asn
                355                 360                 365
Tyr Thr Leu Val Arg Asn Asp Val Pro Val Ser Tyr Leu Ala Gln Ile
    370                  375                 380
His Tyr Val Lys Pro Val Met Leu Ala Pro Thr Leu Asn Gly Leu
385                  390                 395                 400
Ala Thr Tyr Phe Ser Leu Asp Ser Lys Pro Phe Ala Asp Ala Lys Asn
                405                 410                 415
Ala Ala Thr Leu Gly Pro Trp Ala Ala Ser Leu Asp Gly Gly Thr Leu
                420                 425                 430
Ala Ala Asp Asn Phe Ser Gly Gln Ser Leu Gln Leu Asp Ser Arg Val
                435                 440                 445
Asp Ser Tyr Lys Leu Ala Tyr Asn Ala Ala Asp Ile Thr Gln Ser
    450                  455                 460
Pro Gln Phe Thr Ile Gly Phe Trp Phe Arg Thr Asp Cys Ala Gln Gly
465                  470                 475                 480
Asn Gly Thr Gly Glu Pro Ile Leu Ser Asn Lys Asn Tyr Ile Ser Gly
                485                 490                 495
Gly Asn Pro Gly Ile Ala Val Ala Leu Phe Gly Ser Cys Glu Ile Arg
                500                 505                 510
Phe Asn Leu Gly Ser Gly Ser Gly Lys Arg Asp Asp Ile Asn Gly Met
                515                 520                 525
Lys Val Ser Ala Asn Gln Trp Ala Tyr Leu Ala Leu Ser Val Asp Ala
                530                 535                 540
Ala Ala Arg Arg Phe Ser Ala Tyr Val Ile Asp Pro Val Leu Gly Leu
545                  550                 555                 560
Gln Arg Thr Glu Asn Lys Ala Ile Thr Asn Thr Asp Val Thr Lys Leu
                565                 570                 575
```

```
Ala Gly Leu Gly Thr Gly Trp Gly Val Asn Asp Asp Ala Thr His Asn
            580                 585                 590

Tyr Val Gly Asn Asn Pro Gly Ala Leu Lys Gly Val Met Gly Phe Asn
            595                 600                 605

Asp Leu Ala Met Trp Thr Arg Val Leu Ser Leu Asp Glu Leu Lys Ala
            610                 615                 620

Ile Thr Gly Ala Arg Gln Pro Leu Ser Thr Leu Asn Pro
625                 630                 635

<210> SEQ ID NO 8
<211> LENGTH: 594
<212> TYPE: PRT
<213> ORGANISM: Aeromonas caviae

<400> SEQUENCE: 8

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
```

```
            305                 310                 315                 320
        Gly Gly Thr Ala Leu Ser Leu Ala Met Gly Trp Leu Ala Ala Arg Arg
                        325                 330                 335
        Gln Lys Gln Arg Val Arg Thr Ala Thr Leu Phe Thr Thr Leu Leu Asp
                        340                 345                 350
        Phe Ser Gln Pro Gly Glu Leu Gly Ile Phe Ile His Glu Pro Ile Ile
                        355                 360                 365
        Ala Ala Leu Glu Ala Gln Asn Glu Ala Lys Gly Ile Met Asp Gly Arg
                        370                 375                 380
        Gln Leu Ala Val Ser Phe Ser Leu Leu Arg Glu Asn Ser Leu Tyr Trp
        385                 390                 395                 400
        Asn Tyr Tyr Ile Asp Ser Tyr Leu Lys Gly Gln Ser Pro Val Ala Phe
                        405                 410                 415
        Asp Leu Leu His Trp Asn Ser Asp Ser Thr Asn Val Ala Gly Lys Thr
                        420                 425                 430
        His Asn Ser Leu Leu Arg Arg Leu Tyr Leu Glu Asn Gln Leu Val Lys
                        435                 440                 445
        Gly Glu Leu Lys Ile Arg Asn Thr Arg Ile Asp Leu Gly Lys Val Lys
                        450                 455                 460
        Thr Pro Val Leu Leu Val Ser Ala Val Asp Asp His Ile Ala Leu Trp
        465                 470                 475                 480
        Gln Gly Thr Trp Gln Gly Met Lys Leu Phe Gly Gly Glu Gln Arg Phe
                        485                 490                 495
        Leu Leu Ala Glu Ser Gly His Ile Ala Gly Ile Ile Asn Pro Pro Ala
                        500                 505                 510
        Ala Asn Lys Tyr Gly Phe Trp His Asn Gly Ala Glu Ala Glu Ser Pro
                        515                 520                 525
        Glu Ser Trp Leu Ala Gly Ala Thr His Gln Gly Gly Ser Trp Trp Pro
                        530                 535                 540
        Glu Met Met Gly Phe Ile Gln Asn Arg Asp Glu Gly Ser Glu Pro Val
        545                 550                 555                 560
        Pro Ala Arg Val Pro Glu Glu Gly Leu Ala Pro Ala Pro Gly His Tyr
                        565                 570                 575
        Val Lys Val Arg Leu Asn Pro Val Phe Ala Cys Pro Thr Glu Glu Asp
                        580                 585                 590
        Ala Ala

<210> SEQ ID NO 9
<211> LENGTH: 34
<212> TYPE: DNA
<213> ORGANISM: Artificial
<220> FEATURE:
<223> OTHER INFORMATION: Primer

<400> SEQUENCE: 9
gcgcgcattt aaatcagacg actacgtggt gctg                                    34

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ggtacgactc ctatatgcaa                                                    20
```

<210> SEQ ID NO 11
<211> LENGTH: 40
<212> TYPE: DNA
<213> ORGANISM: Artificial
<220> FEATURE:
<223> OTHER INFORMATION: Primer

<400> SEQUENCE: 11
ttgcatatag gagtcgtacc tcgcatcggc gaatggcgca                40

<210> SEQ ID NO 12
<211> LENGTH: 34
<212> TYPE: DNA
<213> ORGANISM: Artificial
<220> FEATURE:
<223> OTHER INFORMATION: Primer

<400> SEQUENCE: 12
gcgcgcattt aaatttgtcg atcaccttgg tgat                     34

<210> SEQ ID NO 13
<211> LENGTH: 34
<212> TYPE: DNA
<213> ORGANISM: Artificial
<220> FEATURE:
<223> OTHER INFORMATION: Primer

<400> SEQUENCE: 13
gcgcgcattt aaatgcacgc cagccgctgt ccac                     34

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ggattctgtg ccgggtggtt                                     20

<210> SEQ ID NO 15
<211> LENGTH: 40
<212> TYPE: DNA
<213> ORGANISM: Artificial
<220> FEATURE:
<223> OTHER INFORMATION: Primer

<400> SEQUENCE: 15
aaccacccgg cacagaatcc cgcgcaagtc gcctgacggg               40

<210> SEQ ID NO 16
<211> LENGTH: 34
<212> TYPE: DNA
<213> ORGANISM: Artificial
<220> FEATURE:
<223> OTHER INFORMATION: Primer

<400> SEQUENCE: 16
gcgcgcattt aaatggcgtt gcgcagcagg tagt                     34

<210> SEQ ID NO 17
<211> LENGTH: 34
<212> TYPE: DNA
<213> ORGANISM: Artificial
<220> FEATURE:
<223> OTHER INFORMATION: Primer

<400> SEQUENCE: 17
gggatgattt aaatgtgtcg ctggcggcca tatc                          34

<210> SEQ ID NO 18
<211> LENGTH: 40
<212> TYPE: DNA
<213> ORGANISM: Artificial
<220> FEATURE:
<223> OTHER INFORMATION: Primer

<400> SEQUENCE: 18
cagcaaggcc gcggccggca atttcctccc cgttggtttt                    40

<210> SEQ ID NO 19
<211> LENGTH: 40
<212> TYPE: DNA
<213> ORGANISM: Artificial
<220> FEATURE:
<223> OTHER INFORMATION: Primer

<400> SEQUENCE: 19
aaaaccaacg gggaggaaat tgccggccgc ggccttgctg                    40

<210> SEQ ID NO 20
<211> LENGTH: 34
<212> TYPE: DNA
<213> ORGANISM: Artificial
<220> FEATURE:
<223> OTHER INFORMATION: Primer

<400> SEQUENCE: 20
gggatgattt aaattcttgc gcatggcgtc gctg                          34

<210> SEQ ID NO 21
<211> LENGTH: 34
<212> TYPE: DNA
<213> ORGANISM: Artificial
<220> FEATURE:
<223> OTHER INFORMATION: Primer

<400> SEQUENCE: 21
gggatgattt aaatgtgtcg ctggcggcca tatc                          34

<210> SEQ ID NO 22
<211> LENGTH: 40
<212> TYPE: DNA
<213> ORGANISM: Artificial
<220> FEATURE:
<223> OTHER INFORMATION: Primer

<400> SEQUENCE: 22
cagcaaggcc gcggccggca atttcctccc cgttggtttt                    40

<210> SEQ ID NO 23
<211> LENGTH: 40
<212> TYPE: DNA
<213> ORGANISM: Artificial
<220> FEATURE:
<223> OTHER INFORMATION: Primer

<400> SEQUENCE: 23
aaaaccaacg gggaggaaat tgccggccgc ggccttgctg                    40

<210> SEQ ID NO 24

```
<211> LENGTH: 34
<212> TYPE: DNA
<213> ORGANISM: Artificial
<220> FEATURE:
<223> OTHER INFORMATION: Primer

<400> SEQUENCE: 24
gggatgattt aaattcttgc gcatggcgtc gctg                                    34

<210> SEQ ID NO 25
<211> LENGTH: 34
<212> TYPE: DNA
<213> ORGANISM: Artificial
<220> FEATURE:
<223> OTHER INFORMATION: Primer

<400> SEQUENCE: 25
gggcccattt aaatcactgc gcttccgctc caac                                    34

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
acggccgcgc gacatccccg                                                    20

<210> SEQ ID NO 27
<211> LENGTH: 40
<212> TYPE: DNA
<213> ORGANISM: Artificial
<220> FEATURE:
<223> OTHER INFORMATION: Primer

<400> SEQUENCE: 27
cggggatgtc gcgcggccgt atccggccgg agcccgtttc                              40

<210> SEQ ID NO 28
<211> LENGTH: 34
<212> TYPE: DNA
<213> ORGANISM: Artificial
<220> FEATURE:
<223> OTHER INFORMATION: Primer

<400> SEQUENCE: 28
gcccggattt aaatgacaaa acggctacgc ccgc                                    34

<210> SEQ ID NO 29
<211> LENGTH: 2004
<212> TYPE: DNA
<213> ORGANISM: Cupriavidus necator H16

<400> SEQUENCE: 29
gtgctggccg ccaccatgat cgccgcactg gcggcaacac tggccggctg cggcggcggc        60
gatgacaccg cgccgacaac cgcaccgaac gacaccacca tcaagacccc gccgcctgcc       120
ggtgccggcg gccgcgcgt gctgctggtc ggcgtggacg tgccaccta tgcccaggtg         180 cagggcgcgc tgctgcggcg cgagctgccc aacctggccc ggctgaacct ggtgcccacc       240
gccaccggcg gcatgcccgg caccatcacc gcgcagccgc gctggacgc gcccagctgg        300 gccacggtgc tgaccggcgc ctgggccaac cgccacggca tcgaagacga taccggcagc       360
accgcactgc aggcccccac cgtattccgc tacctgcgcg cggccggcaa accggcctg        420
```

```
cagcaaggcg catccaccag ttcggggtg ctgccgggcc tgctcaaggc cgagcaggaa      480
gcgggcatgc tcgatacgct ggttgactgc gccgggtcg acagctgcgt cacgcagaac      540
gccgtgcggc aggtgcagtc cggctatggc gtagtgtttg cgcaatacag cgcgccggca      600
caggcggcag aagccggcgg cttcggcaac ggcgcctatg ccacgcccct ggccggcatc      660
gacaaggcgc tgggcgagct gctcggcgcc gtcgcagcgc gcagccaggg gcagccgggt      720
gaagactggc tggtgatggt caccaccagc cacggcctgg atgccaccgg cgccaccacc      780
acggtgccga cggtggagaa ccgcaccgcc ttcctcgcca ccaacaaggc gctcaacggc      840
gcgctggcca aacctggcgc agcagcgccg gacaccccgg cggacctgtc ggcgctgccg      900
accgaagccg atctcgtccc gaccgtgctg gcccacgccg gcgtggcgct tgacccggcc      960
accacgcggc tggacggttc ggcgctgacc accgccaacg caggcgtgcg agccatcggc     1020
gccagcatca gccagtacaa cgacgccatc acgctgagct ggcagaaccc gaccgaagcc     1080
ttcggcgtca cccgcgtgct gcgcgacggc gtgcagatcg cctcgctggg acctgaggtg     1140
cggcagttca ccgacaaggc cttcaacatg ccacgggcc tgtaccagtt caactacacg      1200
ctggtgcgca atgacgtgcc ggtgtcgtac ctggcgcaga tccactacgt caagccggtc     1260
atgctggcgc cgacgctgct caatggcctg gccacgtact tcagcctcga cagcaagccg     1320
ttcgccgatg cgaagaacgc cgccacgctc ggcccgtggg cggcaagcct tgacggcggc     1380
acgctggctg ccgacaactt cagcggccag tcgctgcagc tggactcgcg tgtcgacagc     1440
tacaagctgg cgtacaacgc tgccgccgat atcacgcaga gcccgcagtt caccatcggc     1500
ttctggttcc gcaccgactg cgcccagggc aacggcaccg gcgagcccat cctgtccaac     1560
aagaactaca tctcgggcgg caaccccggc attgccgtgg cgctgttcgg cagctgcgag     1620
atccgtttca acctgggcag cggcagcggc aagcgcgacg acatcaacgg catgaaggtg     1680
tcggccaacc agtgggccta cctggcgctg tcggtcgacg cggcagccag gcgcttcagc     1740
gcctatgtca tcgatccggt gctgggcctg cagaggaccg agaacaaggc gatcaccaat     1800
accgacgtga ccaagctggc cgggctcggc accggctggg gcgtgaacga cgatgccacg     1860
cacaactacg tgggcaacaa ccccggcgcg ctcaagggcg tgatgggctt caacgacctg     1920
gcgatgtgga cgcgcgtgct gtcgctggac gagctgaagg ccatcaccgg cgcacgccag     1980
ccgctgtcca cgctgaatcc ttaa                                           2004

<210> SEQ ID NO 30
<211> LENGTH: 34
<212> TYPE: DNA
<213> ORGANISM: Artificial
<220> FEATURE:
<223> OTHER INFORMATION: Primer

<400> SEQUENCE: 30
gggcccattt aaatcaccgg ctacgcgcag atct                                 34

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
ggcgtggtct cctcggtttt                                                 20
```

<210> SEQ ID NO 32
<211> LENGTH: 40
<212> TYPE: DNA
<213> ORGANISM: Artificial
<220> FEATURE:
<223> OTHER INFORMATION: Primer

<400> SEQUENCE: 32
aaaaccgagg agaccacgcc gcacgctgcc aggcccgggc                40

<210> SEQ ID NO 33
<211> LENGTH: 34
<212> TYPE: DNA
<213> ORGANISM: Artificial
<220> FEATURE:
<223> OTHER INFORMATION: Primer

<400> SEQUENCE: 33
cgcgcgattt aaatgccgtg gccgtagagc ttga                      34

<210> SEQ ID NO 34
<211> LENGTH: 1281
<212> TYPE: DNA
<213> ORGANISM: Cupriavidus necator H16

<400> SEQUENCE: 34
atgcaacccc ttcgactgat cctgccgcgg gcctcgcgcc catccacggt gccggcgcgt    60
gcgctggccg tggccgccac cgccatgctc gccgcctgcg gtggcggcgg cggcgacgac   120
gcgccgtcca cgccggccgc ggtgcagacg cggctgtgcc cggcagcgct cgactactcc   180
accacctta ccggcggcac cggctccggc gagctggtga aggtgcagat cgacaccacc   240
aaaaagacct ggcaggtgac cttcgtggac tcgtcggtgc cgcgccagac cggcaccgtg   300
cagcccacgc gcagcgatcc caccaacggg cagaacgtga tgcgcggcac gctgaaggcg   360
gagacggggt tgccgaccga gaagctcaac cagtgcgcgt tcgagctgag cggcgccagc   420
ctcgatccga accgtccggc caagctcttc gtcggcgaag gcgtggtggg cggcaccatc   480
ccgggcgcgc gcatccagtt caacggcgtg ctgggcgccg cgcgcggtgcc ggacaccacc   540
ttcccgtatt tccagttcat cggcttcgcg cagaccgaga ccgacctgtc gaagattgcc   600
ggccagtaca acggcacggg cttccacgag gtgccgtcca agcagttcca gctggtggcg   660
caggactacc gcatggcgct ggctgccgat ggttccttca ccgtctgcga caacgccacc   720
aacacgtgcg agcgcaaggg caacaacttc gtgccgcagg cgagcggcgc gctgctgtcg   780
accaactaca aggccgagag ccagccgccc acgctgggcg gcacgctggg caaggcctac   840
ctgatcgtgg gcaagctgcg cggccagctg gtgccggtca tgatccgcgt gggctatgcc   900
aatgactcgc tcgccaacgg cccgcttggt gccgacgacg agatcggcat cggcatgatg   960
gcgccggcgg tagcgcttac tgaaggcacg gtcaacggcg aatacgtcgg cgtggacagc  1020
aacttcaact accgcgtgac ggcactggtc ggcgccgcgg ccaccatgat ggatccgttc  1080
cggccgcatg atgcctcgct cgccatcccg taccggctgg atttctcgca gcaggtgccg  1140
ggcgtggtcc gcacgtcgcg gcgcgatgcg cctgcaggct cggcgccgac cggcaagctg  1200
atgttcaccg gcggcgtgtt cggcttcctg gaacagcgcg acagcggccc gtacttcacc  1260
gtcggcgcat tcgtgcagta a                                           1281